(12) United States Patent
Giselbrecht et al.

(10) Patent No.: US 6,486,358 B1
(45) Date of Patent: Nov. 26, 2002

(54) PROCESS FOR THE PURIFICATION AND FORMULATION OF O-PHTHALALDEHYDE

(75) Inventors: Karlheinz Giselbrecht, Pasching (AT); Walter Raml, Hellmonsödt (AT); Rudolf Hermanseder, Pennewang (AT)

(73) Assignee: DSM Fine Chemicals Austria NFG GmbH & CO KG, Linz (AT)

( * ) Notice: Subject to any disclaimer, the term of this patent is extended or adjusted under 35 U.S.C. 154(b) by 0 days.

(21) Appl. No.: 10/144,887

(22) Filed: May 15, 2002

(30) Foreign Application Priority Data

May 15, 2001 (AT) ............................................. 768/2001

(51) Int. Cl.⁷ ............................................. C07C 45/00
(52) U.S. Cl. ............................................. 568/438
(58) Field of Search .......................... 568/438

(56) References Cited

FOREIGN PATENT DOCUMENTS

| EP | 0 147 593 | 7/1985 |
|---|---|---|
| EP | 0 522 312 | 1/1993 |
| EP | 0 839 789 | 5/1998 |

*Primary Examiner*—Alan Siegel
(74) *Attorney, Agent, or Firm*—Wenderoth, Lind & Ponack, L.L.P.

(57) ABSTRACT

Improved process for the purification and formulation of o-phthalaldehyde in which crude o-phthalaldehyde, obtained by cleavage of an acetal of o-phthalaldehyde by means of acidic hydrolysis, is, optionally by adding an aqueous basic solution, adjusted to a pH of from 1 to 8, and then, after phase separation has taken place, water is distilled off from the phase which contains the aldehyde with very short thermal stress of less than 1 minute at a pressure of between 100 mbar and atmospheric pressure and a temperature of from room temperature to 180° C. on a thin-layer overhead evaporator and o-phthalaldehyde is then stripped off from the distillation bottom which remains with very short thermal stress of less than 1 minute at a pressure of from 0.5 to 50 mbar and a jacket temperature of from 80 to 80° C. via a thin-layer evaporator and the resulting o-phthalaldehyde melt is pelleted at atmospheric pressure and a temperature of from 60 to 80° C., giving pale yellow o-phthalaldehyde in high purity and storage-stable form.

8 Claims, No Drawings

PROCESS FOR THE PURIFICATION AND FORMULATION OF O-PHTHALALDEHYDE

Phthalaldehydes, such as o-phthalaldehyde (OPA), are used in many fields, for example as intermediates for the preparation of dyes, optical brighteners or special polymers, in the biocide or photo industry, and for the synthesis of pharmachemicals. For this reason, a number of preparation variants have already been described. Thus, o-phthalaldehyde (OPA) can, for example, be obtained according to EP-B-0 147 593 by ozonolysis of naphthalene in methanol and catalytic reduction of the resulting peroxides with subsequent extraction or crystallization. The disadvantage of this process is that the ester which forms as byproduct can only be separated off from the OPA with difficulty and inadequately.

In addition, OPA is a reactive compound which is not thermally and oxidatively stable and which, upon prolonged storage has a tendency to block, as a result of which lengthy detachment processes are required, which may lead to discoloration of the OPA.

In order to protect the aldehyde against undesired reactions, EP-A1-0522 312 has described the option of using o-phthalaldehyde tetraalkyl acetals, prepared by electrochemical oxidation, as donor compounds.

Furthermore, EP-B-0 839 789 discloses the conversion of OPA by acid-catalyzed acetal formation with subsequent distillation into a suitable donor compound, such as, for example, into a dialkoxyphthalan or tetraalkyl acetal, from which, if necessary after complete acetal cleavage by acidic hydrolysis, crude OPA is obtained with purities of greater than 99.5%.

Since crude OPA, for example prepared in accordance with EP-B-0 839 789, however, has a red-orange color, it must then still be recrystallized following decoloration with, for example, activated carbon or tonsil.

The fine OPA powder having a melting point of 57° C. which is obtained by crystallization likewise has a tendency to block. In addition, the different batches do not have constant color and quality.

An object of the present invention was therefore to find an improved process for the isolation and formulation of OPA, by which crude OPA can be purified in a simple and safe manner and virtually quantitatively and be converted into a storable form which does not block even after years.

Surprisingly, this object was achieved by a distillation of the crude thermally unstable o-phthalaldehyde obtained from the acetal cleavage on a thin-layer evaporator with subsequent pelleting.

Accordingly, the invention provides an improved process for the purification and formulation of o-phthalaldehyde wherein crude o-phthalaldehyde, obtained by cleavage of an acetal of o-phthalaldehyde by means of acidic hydrolysis, a) is, optionally by adding an aqueous basic solution, adjusted to a pH of from 1 to 8, and then, after phase separation has taken place, b) water is distilled off from the phase which contains the aldehyde with very short thermal stress of less than 1 minute at a pressure between 100 mbar and atmospheric pressure and a temperature of from room temperature to 180° C. on a thin-layer evaporator and c) o-phthalaldehyde is then stripped off overhead from the distillation bottom which remains with very short thermal stress of less than 1 minute at a pressure of from 0.5 to 50 mbar and a jacket temperature of from 80 to 180° C. via a thin-layer evaporator and d) the resulting o-phthalaldehyde melt is pelleted at atmospheric pressure and a temperature of from 60 to 80° C., giving pale yellow o-phthalaldehyde in high purity and storage-stable form.

In the novel process, crude o-phthalaldehyde (OPA) is purified and converted into a storage-stable form.

The starting material used is crude OPA which is obtained by cleavage of an OPA acetal. OPA acetals, such as, for example, dialkoxyphthalans or tetraalkyl acetals, can be prepared, for example, analogously to EP-A1-0522 312 or EP-B-0 839 789.; The cleavage of the acetals likewise takes place by the customary route, analogously to the prior art, for example by acidic hydrolysis at a pH between 0 and 7, preferably between 0 and 3 by means of mineral acids such as HCl, $H_2SO_4$, $H_3PO_4$, or organic acids, such as acetic acid, formic acid and p-toluenesulfonic or methanesulfonic acid. The reaction temperature is preferably between room temperature and 100° C. The alcohol which is eliminated and optionally the acid is then distilled off under reduced pressure.

The resulting crude OPA to be purified has a content of more than 99.5%. According to the invention, an aqueous basic solution is then optionally added so that a pH between 1 and 8, preferably between 2 and 7, is established. Suitable bases are carbonates, such as, for example, bicarbonates or dilute hydroxide solutions, such as, for example, NaOH, KOH etc.

The aqueous basic solution is added at atmospheric pressure and at a temperature of from 40 to 95° C., preferably from 50 to 70° C. Phase separation then takes place, the OPA being present in the lower heavy phase which has a water content of from 0.5% to 3%, preferably 1.0 to 2%. Water is removed from the OPA-containing phase by distillation on a thin-layer evaporator with very short thermal stress by distilling off water or aqueous OPA.

Suitable thin-layer evaporators are falling-film evaporators, short-path evaporators etc. Preference is given here to using a falling-film evaporator.

The first distillation step takes place at a pressure of 100 mbar to atmospheric pressure, preferably at a pressure of from 100 to 250 mbar and particularly preferably at a pressure of from 150 to 200 mbar.

The reaction temperature here is a jacket temperature between room temperature and 180° C., preferably between 100° C. and 180° C.

The residence time in the thin-layer evaporator is very short and is between 10 seconds and <1 minute.

In this distillation step, water is distilled off, but in most cases some OPA is also codistilled. This aqueous OPA can be introduced in a next batch, again with pH adjustment using aqueous basic solution, so that a loss in the yield of OPA is prevented.

The material which remains is the distillation bottom which comprises the majority of brown colored OPA, with a water content of now only 0.01 to 0.4%, preferably up to 0.1%, and a content of more than 99.5%.

This distillation bottom is then subjected again to distillation with very short thermal stress on a thin-layer evaporator, OPA this time being drawn off overhead.

Suitable thin-layer evaporators here are likewise falling-film evaporators, short-path evaporators etc. Preference is given here to using a short-path evaporator. The residence time in the thin-layer evaporator is very short and is between 10 sec and <1 minute.

The second distillation step takes place at a pressure of from 0.5 to 50 mbar, preferably at a pressure of from 3 to 15 mbar, and particularly preferably at a pressure of from 5 to 10 mbar.

The temperature here is a jacket temperature between 80° C. and 180° C.

The distillate comprises the purified, now pale yellow OPA with a content of more than 99.5%. The bottom in which, however, still relatively large amounts of OPA are also present, can be metered in in a subsequent batch to avoid losses in yield.

The distillation is then followed by pelleting at a temperature of from 60° C. to 80° C., preferably between 60 and 70° C. and atmospheric pressure.

During pellet bottling, the temperature is cooled to below 30° C.

The purification process according to the invention produces OPA in a storage-stable form which does not form clumps even after several months. In addition, OPA purified in accordance with the invention has a uniform color, while a different coloration arises in the case of OPA which is purified by crystallization. Furthermore the purification process according to the invention prevents losses in the yield of OPA.

EXAMPLE 1

Crude OPA from the acetal cleavage according to EP-B-0 839 789 with a GC content of >99.5 GC area % was admixed with 300 ml of water and, at 500° C. to 600° C. adjusted from pH 3 to pH 7 with 10% strength bicarbonate solution. The phases then separated very well and very quickly. The lower 670 g-heavy crude OPA phase had a water content of 1.5%. Water was removed from this phase on a thin-layer evaporator (TE) (0.12 $m^2$ surface area) and with very short thermal stress (<1 minute) by distilling off aqueous OPA which was introduced in the next batch, again with pH adjustment (TE parameters: 180 mbar, 7 bar vapor, 50 l/h of $N_2$ in countercurrent and 400 ml/h of crude OPA charge). 617 g of brown colored crude OPA with a water content of 0.09% and a content of <99.5% collected in the bottom.

This crude OPA TE bottom was again passed via the TE, but this time overhead (TE parameters: 9 mbar, 7 bar vapor, 50 l/h of $N_2$ in countercurrent and 617 g/h of crude OPA charge). 580 g of pale yellow OPA (85% yield) with a GC content of >99.5% collected in the distillate. The bottom (37 g) still comprised at least 85% OPA which was introduced in the next TE batch. In order to give the OPA melt a shape and to prevent packing of the OPA, pelleting was carried out at atmospheric pressure and 65° C.; pellet bottling was carried out at 250° C.

What is claimed is:

1. An improved process for the purification and formulation of o-phthalaldehyde, wherein crude o-phthalaldehyde, obtained by cleavage of an acetal of o-phthalaldehyde by means of acidic hydrolysis, a) is, optionally by adding an aqueous basic solution, adjusted to a pH of from 1 to 8, and then, after phase separation has taken place, b) water is distilled off from the phase which contains the aldehyde with very short thermal stress of less than 1 minute at a pressure between 100 mbar and atmospheric pressure and a temperature of from room temperature to 180° C. on a thin-layer evaporator and c) o-phthalaldehyde is then stripped off overhead from the distillation bottom which remains with very short thermal stress of less than 1 minute at a pressure of from 0.5 to 50 mbar and a jacket temperature of from 80 to 180° C. via a thin-layer evaporator and d) the resulting o-phthalaldehyde melt is pelleted at atmospheric pressure and a temperature of from 60 to 80° C., giving pale yellow o-phthalaldehyde in high purity and storage-stable form.

2. The process as claimed in claim 1, wherein, in step a), a pH of between 2 and 7 is established by adding an aqueous carbonate, NaOH or KOH solution.

3. The process as claimed in claim 1, wherein the addition of the aqueous basic solution takes place at a temperature between 40° C. and 95° C.

4. The process as claimed in claim 1, wherein, in step b), the distillation is carried out at a pressure between 100 and 250 mbar and a jacket temperature between 100° C. and 180° C.

5. The process as claimed in claim 1, wherein, during the distillation in step b), o-phthalaldehyde optionally codistilled with the water is optionally metered in as aqueous o-phthalaldehyde solution in a next batch in step a).

6. The process as claimed in claim 1, wherein, in step c), o-phthalaldehyde is distilled off overhead at 3 to 15 mbar from the distillation bottom obtained by step b).

7. The process as claimed in claim 1, wherein the distillation bottom which remains from step c), which optionally still comprises o-phthalaldehyde, is optionally metered in a the next batch in step c).

8. The process as claimed in claim 1, wherein, in step d), the pelleting takes place at a temperature between 60° C. and 70° C., after which, during pellet bottling, the temperature is cooled to below 30° C.

* * * * *